(12) United States Patent
Piquer et al.

(10) Patent No.: US 6,326,504 B1
(45) Date of Patent: Dec. 4, 2001

(54) PROCEDURE TO EXTRACT NATURAL PRODUCTS

(75) Inventors: Miguel Blasco Piquer; Bautista Enrique Mira Ferri; Juan Gabriel Martinez Fuentes; Gerardo Faus Fortea; Sebastian Subirats Huerta, all of Valencia (ES)

(73) Assignee: Asociacion de Investigacion del la Industria Agroalimentaria, Paterna (ES)

( * ) Notice: Subject to any disclaimer, the term of this patent is extended or adjusted under 35 U.S.C. 154(b) by 0 days.

(21) Appl. No.: 09/154,030

(22) Filed: Sep. 16, 1998

Related U.S. Application Data

(63) Continuation-in-part of application No. PCT/ES97/00015, filed on Jan. 28, 1997.

(51) Int. Cl.⁷ ........................................................ C07C 1/00
(52) U.S. Cl. ................................................................ 554/11
(58) Field of Search .................................................. 584/11

(56) References Cited

U.S. PATENT DOCUMENTS

| 5,110,509 | | 5/1992 | Peter et al. ............................ 554/184 |
| 5,210,240 | * | 5/1993 | Peter et al. ............................ 554/11 |

* cited by examiner

*Primary Examiner*—Deborah D. Carr
(74) *Attorney, Agent, or Firm*—Maria Parrish Tungol

(57) ABSTRACT

Process for high pressure extraction of organic products from vegetable or animal matrices or extracts thereof wherein the process is carried out in the presence of one or more liquid solvents and one or more supercritical fluids wherein the proportion of the supercritical fluid is less than 50% by weight of the total weight of the solvent and the supercritical fluid.

7 Claims, No Drawings

PROCEDURE TO EXTRACT NATURAL PRODUCTS

This application is continuation-in-part of International Application PCT/ES97/00015, with an international filing date of Jan. 28, 1997, now pending.

FIELD OF THE INVENTION

This invention relates to a procedure to extract organic products from vegetable or animal matrices, or their extracts, by means of high-pressure extraction using conventional liquid solvents and in the presence of small amounts of supercritical fluids.

BACKGROUND OF THE INVENTION

Several methods of extracting organic products from vegetable or animal matrices are disclosed in the prior art such as JP 02235997 (Preparation of alga aromas by extraction with supercritical or semi-critical carbon dioxide in the presence of water or alcohol), U.S. Pat. No. 4,675,198 (Extraction of aromas from vegetable products using liquid or supercritical extractors), JP 62036178 (Extraction and separation of organic compounds of grape skin), DE 2737794 (Decaffeinisation of coffee by extraction with a solvent), DE 2638383 (Elimination of caffeine from coffee). There are also a significant number of publications which disclose similar processes, although it should be borne in mind that these processes follow the strategy of using supercritical $CO_2$ in the presence of small amounts or organic and/or inorganic solvents.

A process for the extraction of oils from oil-containing solid vegetable material by means of a mixture consisting of a supercritical gas and a subcritical entraining agent is disclosed in U.S. Pat. No. 5,210,240, herein incorporated by reference.

There are many disadvantages with the current methods, such as the need to use large equipment and a high level of energy to produce relatively small amounts of product. This is because solvents are used with small solubilities or solvents which are not saturated when leaving the extractor as a result of the slow kinetics of extraction involved, and therefore the consumption of solvent per unit of extracted active product mass, is very high.

With current techniques, substances are being extracted from vegetable matrices with pure or modified supercritical $CO_2$ with a small proportion of organic solvent (ethanol, acetone, hexane, methanol, water, etc.), which is always in a proportion less than 50%.

SUMMARY OF THE INVENTION

The present invention relates to a high pressure process for extraction of organic products from vegetable or animal matrices or extracts thereof wherein the process is carried out in the presence of one or more liquid solvents and one or more supercritical fluids wherein the proportion of the supercritical fluid is less than 50% by weight of the total weight of the solvent and the supercritical fluid.

DETAILED DESCRIPTION OF THE INVENTION

The process of the invention includes macerating the initial material at pressures of between 50 and 500 bar, in a solvent such as water, hydrocarbon, alcohol, ketone, ether, carbon halide or a mixture thereof, containing a supercritical fluid (SCF) such as $CO_2$, propane, ethane or mixtures thereof in a proportion of less than 50% by weight of the total weight of the solvent and the SCF. The high working pressure causes the penetration of SCF, as it reduces its viscosity and increases diffusivity. This increase in diffusivity and reduction in viscosity causes the mobility of SCF through the inside of the cells and allows substances to be extracted at a much higher speed and in greater quantities than the conventional extractions or in other existing extraction patents to data.

Apart from atmosphere extraction which avoids oxidation, it is also carried out at such moderate temperatures, slightly higher than room temperature, which drastically reduces the risk of decomposition of heat-labile products.

The extraction mechanism means that the product extracted by the SCF is solvated quickly with traditional solvent, setting a balance between solute-SCF-conventional solvent which allows extraction to be performed at all times with the same levels of effectiveness and performance as at the start of the process. There is a continuous transfer of matter from the cells to the conventional solvent, using an intermediate phase formed by the SCF.

The innovation of the process over existing processes lies in the fact that proportions between SCF and conventional solvent are inverted, meaning that the resulting mixture is not an SCF but a pressure liquid or a mixture of phases. This process means that the main solvent is not an SCF but ethanol, water or other solvents, which are found in greater proportions. The SCF does not act as a solvent but as a transport vehicle between the vegetable matrix and the solvent.

The procedure according to the invention minimizes extraction time, reduces the solvent/solute ratio and therefore reduces pumping costs, the consumption of solvent and costs for its later recuperation. As quick extraction kinetics are present, the volume of the extractor is reduced for a certain production, or the production increases for a determined volume of extraction.

This type of extraction can be applied to the extraction of organic products such as essential oils, dyes, alkaloids, lipids, oils, waxes, proteins, fatty acids, aromas, spices, isoprenoids, steroids, carotenes, or active pharmaceutical principles present in, or originating from extracts provided by the technique, such as oleoresin or adsorbate, or present in or originating from biological matrices, such as orange skin, paprika, grape skin, coffee, tea, medicinal plants, seeds, carrot or fish viscera.

The solvents that can be used in the process of the invention are those solvents that are conventionally used to extract organic products from vegetable or animal matrices or extracts thereof. Examples of such solvents include water, ethanol, and hexane. Preferred solvents are pentane, hexane, dichlorfluoromethane, chlorofuluromethane, dichloromethane, dimethylethere, ethylmethylether, diethylether, methanol, ethanol, acetone, ethyl butyl ketone, or mixtures thereof.

Preferred SCF's include carbon dioxide, carbon anhydride, methane, ethane, propane, or mixtures thereof. The proportion of SCF to solvent less than 50% by weight based on the total weight of the SCF and solvent. The proportion of SCF to solvent is preferably between about 7 to about 35% by weight, most preferably about 11 to about 26 % by weight. the higher concentrations of SCF are preferred when the animal or vegetable matrix is porous or akin. The lower concentrations of SCF are preferred if the matrix is more compact and less porous.

The process according to the invention is performed at pressures of between 50 and 500 bar, preferably between about 150 to about 280 bar. The time required to perform this operation is generally between about 0.25 and about 20 hours, preferably between about 0.5 and about 5 hours, most preferably between about 15 minutes and about 2 hours. The extraction temperature is typically less than 90° C., preferably between about 40° C. and about 80° C.

The extracted product which is dissolved in the solvent is collected after depressurization. This technique can be combined with a separation phase which allows the extract to be recuperated or fractionated. This recuperation or fiactionation can be carried out following any process offered by the technique and known in the prior art.

Below we detail, as examples, the results obtained by applying the process according to the invention to different matrices.

EXAMPLE 1

Extraction of Oleoresin from Paprika 140 gr. of ground paprika, 320 gr. of ethanol and 60 gr. of $CO_2$ are mixed for 30 minutes at 250 bar and 40° C. The extract is concentrated by vacuum evaporation. 42 gr. of oleoresin are obtained.

EXAMPLE 2

Extraction of Malvidin from Grape Skin 100 gr. of grape skin, 280 gr. of ethanol and 150 gr. of $CO_2$ are mixed for 30 minutes at 150 bar and 80° C. The extract is concentrated by vacuum evaporation. 125 mg. of malvidine are obtained, approximately 70% of the total. This extract is of a very aromatic nature, which proves that the aromas present in the skin are also recuperated during extraction.

EXAMPLE 3

Extraction of Essential Oil, Carotenes and Flavonoids of Orange Skin 150 gr. of dehydrated orange skin, 250 gr. of ethanol and 20 gr. of $CO_2$ are mixed for 30 minutes at 50 bar and 70° C. The extract is concentrated by vacuum evaporation. Nine gr. of oleoresin is obtained, composed of carotenes and flavonoids of the orange skin together with some pectins, free from degradation products, which are very aromatic and stable.

EXAMPLE 4

Extract of Oil From Grape Seeds 77.6 gr. of finely ground grape seeds, 225 gr. of hexane and 60 gr. of $CO_2$ are mixed for one hour at 280 bar and 40° C. The extract is concentrated by means of vacuum evaporation. The dry extract totals 9.25% of the total weight of the seeds used, its composition being: 73% of linoleic acid, 16% in oleic acid, 8% in palmitic acid, 3% stearic acid and 0.3% linolenic acid.

EXAMPLE 5

Extraction of Orange Albedo Pectins 100 gr. of diy and finely ground albedo, 350 gr. of acidified water with nitric acid up to pH 2 and 40 gr. of $CO_2$ are mixed for one hour at 280 bar and 80° C. The extract is concentrated by vacuum evaporation. Ethanol is added to the residue after water evaporation, with which 1.3 gr. of pectins are precipitated.

EXAMPLE 6

Extraction of Oil From Fishmeal 200 gr. of fishmeal, 170 gr. of hexane and 60 gr. of $CO_2$ are mixed for one hour at 250 bar and 50° C. The extract is concentrated by vacuum evaporation. 13 gr. of oil are obtained. The composition of this oil is: 6% myristic acid, 19% palmitic acid, 7% palmitoleic acid, 19% oleic acid, 8% EPA, 8% DHA, 12% non-unidentified fatty acid (owing to lack of reference), another 12% of another non-identified fatty acid (owing to lack of reference), and the remaining 9% composed of myristoleic, pentadecanoic, stearic, heptadecanoic, linoleic and linolenic acids. 1,209 ppm of vitamin A, 122 ppm of vitamin E and small amounts of other vitamins were also found.

EXAMPLE 7

Recuperation of Oil Adsorbed by Decolorant Earth used in Refining this Oil 200 gr. of material with a composition of 76 gr. of adsorption earth, 40 gr. of moisture and 84 gr. of adsorbed olive oil are mixed with 100 gr. of hexane and 40 gr. of $CO_2$ for 30 minutes at 280 bar and 40° C. The extract is concentrated by vacuum evaporation. 68 gr. of edible quality olive oil are obtained.

EXAMPLE 8

Extraction of Essential Oil from Rosemary 100 gr. of dehydrated rosemary, 200 gr. of hexane and 60 gr. of $CO_2$ are mixed for 30 minutes at 150 bar and 40° C. The extract is concentrated by vacuum evaporation. 5.7 gr. of oil are obtained.

EXAMPLE 9

Extraction of Antioxidants from Rosemary 100 gr. of dehydrated rosemary, 200 gr. of water and 60 gr. of $CO_2$ are mixed for 30 minutes at 150 bar and 40° C. The extract is concentrated by vacuum evaporation. 5.5 gr. of water-soluble extract are obtained.

EXAMPLE 10

Extraction of Essential Oils and Oleoresin from *Curcuna longa* Rhizome 125 gr. of *Curcuma longa* rhizome, 450 gr. of azeotropic ethanol and 100 gr. of $CO_2$ are mixed for 30 minutes at 250 bar and 45° C. The extract is concentrated by vacuum evaporation. 6.4 gr. of oleoresin are obtained, which contain 2.9 gr. of curcumin, equivalent to 46% of curcumin present in the initial rhizome.

What is claimed is:

1. Process for high pressure extraction of organic products from vegetable or animal matrices or extracts thereof wherein the process is carried out in the presence of one or more liquid solvents and one or more supercritical fluids wherein the proportion of the supercritical fluid to liquid solvent is between about 7% to about 26% by weight based on the total weight of the solvent and the supercritical fluid.

2. Process according to claim 1 wherein the proportion of the supercritical fluid to liquid solvent is between about 7% to about 11% by weight based on the total weight of the solvent and the supercritical fluid.

3. Process according to claim 1 wherein the extraction time is between about 15 minutes and about 2 hours.

4. Process according to claim 1 wherein the extraction temperature is between about 40° C. and about 80° C.

5. Process according to claim 1 wherein the solvent is selected from the group consisting of water, hydrocarbon, alcohol, ketone, ether, carbon halide, pentane, hexane, dichlorfluoromethane, chlorofuluromethane, dichloromethane, dimethylethere, ethylmethylether, diethylether, methanol, ethanol, acetone, ethyl butyl ketone, or mixtures thereof.

6. Process according to claim 1 wherein the supercritical fluid is selected from the group consisting of $CO_2$, propane, ethane, carbon anhydride, methane, ethane, propane, or mixtures thereof.

7. Process for high pressure extraction of organic products from vegetable or animal matrices or extracts thereof comprising mixing an organic product from vegetable or animal matrices or extracts thereof with one or more liquid solvents and one or more supercritical fluids so that the resulting extraction mixture is a mixture of phases and the proportion ol the supercritical fluid is between about 11% to about 26% by weight based on the total weight of the solvent and the supereritical fluid.

* * * * *